United States Patent [19]

Abt

[11] Patent Number: 4,641,655
[45] Date of Patent: Feb. 10, 1987

[54] THERAPEUTIC COOLING WRAP

[76] Inventor: Nancy G. Abt, 9397 Midnight Pass Rd., Apt. 404S, Sarasota, Fla. 34242

[21] Appl. No.: 761,882

[22] Filed: Aug. 2, 1985

[51] Int. Cl.$^4$ ............................................... A61F 7/02
[52] U.S. Cl. .................................. 128/380; 62/259.3; 128/403; 383/901
[58] Field of Search ............... 128/384, 402, 403, 380; 62/259.3; 383/901

[56] References Cited

U.S. PATENT DOCUMENTS

| | | | |
|---|---|---|---|
| 1,567,931 | 12/1925 | Epler | 128/402 |
| 2,562,121 | 7/1951 | Poux. | |
| 3,429,138 | 2/1969 | Goldmerstein | 62/259.3 |
| 3,882,867 | 5/1975 | Moran | 128/402 X |
| 3,889,684 | 6/1975 | Lebold | 128/403 |
| 3,980,070 | 9/1976 | Krupa | 128/403 X |
| 4,372,318 | 2/1983 | Viesturs | 128/403 |
| 4,381,025 | 4/1983 | Schooley | 128/402 X |
| 4,503,560 | 3/1985 | Bourne | 383/901 X |
| 4,517,972 | 5/1985 | Finch, Jr. | 128/156 |
| 4,576,169 | 3/1986 | Williams | 128/402 |

FOREIGN PATENT DOCUMENTS 718686  9/1965  Canada ................................. 128/380

Primary Examiner—Anton O. Oechsle
Attorney, Agent, or Firm—Charles J. Prescott; Raymond H. Quist

[57] ABSTRACT

A cooling wrap is designed for tying around the neck of a person while performing vigorous activity in hot weather. A closable bag for containing a frozen water medium is stitched in a pouch formed in a strip of water pervious fabric. The strip of fabric is further stitched to form tying straps on both ends of the pouch. A pad of open-pored foam is secured in the bag to insulate the neck from severe cold while still permitting the controlled dispensing of water to the neck. The frozen water medium may be ice, but is preferably open-pored foam which has been saturated with water and frozen.

10 Claims, 6 Drawing Figures

U.S. Patent  Feb. 10, 1987  4,641,655
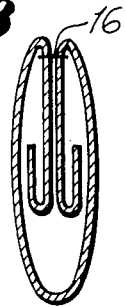
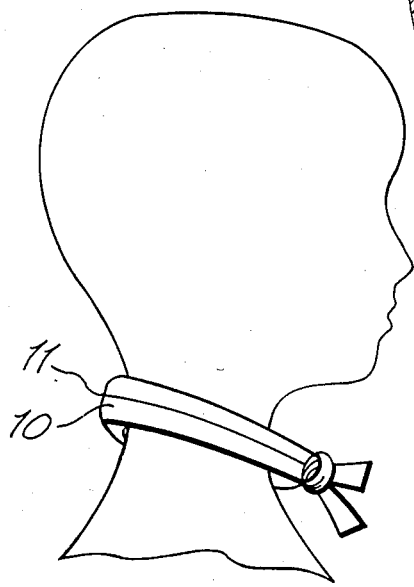
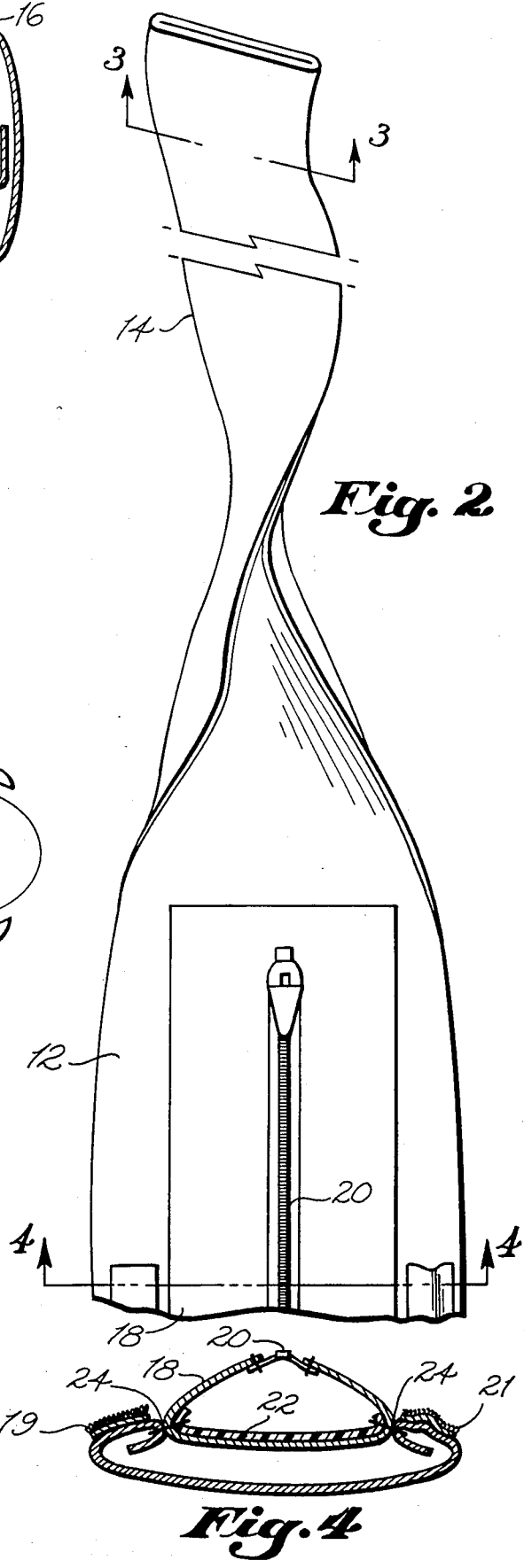
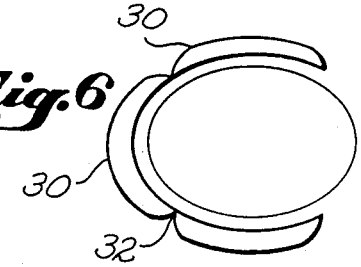
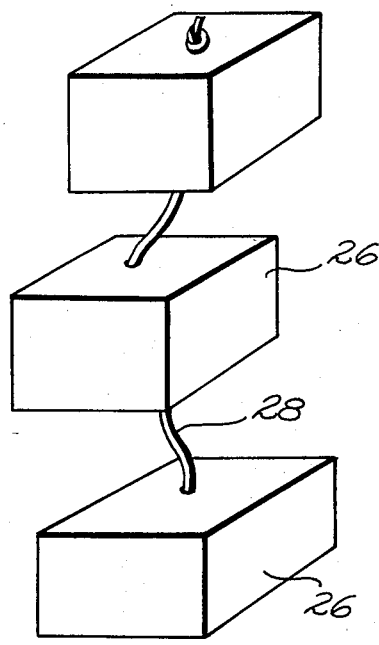

THERAPEUTIC COOLING WRAP

BACKGROUND OF THE INVENTION

1. Field of the Invention

This invention relates generally to a wrap which may be worn about the neck while engaged in vigorous activity in hot weather, and more particularly to a cooling wrap to which heat will be transferred from the neck of the wearer and which will dispense controlled amounts of water to the neck.

2. Description of the Prior Art

The beneficial effects of the application of wet or dry cold compresses to the body in hot weather have long been recognized. The use of such compresses has generally been on patients lying in bed or otherwise inactive. Those involved in vigorous activity such as tennis, golf, running, gardening, etc. in the hot sun have resorted to breaks in which wet towels or water are applied to the body, that is, when they are relatively inactive. Even when compresses have been provided with straps for tying them on the body, it has not been suggested that the compresses will remain in position during vigorous activity.

It is therefore an object of this invention to provide a cooling wrap which can be used while one is engaged in sports or other vigorous activities in a hot environment.

It is a further object of this invention to provide a cooling wrap which will retain a frozen water medium to which body heat can be transferred.

It is also an object of this invention to provide a cooling wrap which will dispense controlled amounts of water on the body.

SUMMARY OF THE INVENTION

A cooling wrap has a central pouch section with straps at either end for tying the wrap around the neck of the wearer. The pouch section has secured therein a bag having closure means. The bag contains an open-pored foam pad and is intended to receive frozen water medium such as ice or preferably open-pored foam which has been saturated with water and frozen. This "frozen foam" and the foam pad retard the melting of the ice and also dispense the resulting water in a regulated manner. The foam pad also provides a comfortable coolness rather than severe cold.

BRIEF DESCRIPTION OF THE DRAWINGS

FIG. 1 represents the cooling wrap of this invention in use;

FIG. 2 is a detail of the cooling wrap showing a representative portion;

FIG. 3 is a cross-section of the strap portion of a cooling wrap taken on the line 3—3 of FIG. 2;

FIG. 4 is a cross-section of the pouch portion of a cooling wrap taken on line 4—4 of FIG. 2;

FIG. 5 is a representation of one form of "frozen foam"; and

FIG. 6 is a representation of another form of "frozen foam".

DESCRIPTION OF THE PREFERRED EMBODIMENT

Referring to FIG. 1, a cooling wrap 10 in accordance with the invention is illustrated tied about the neck of a wearer. Line 11 represents the juncture formed when the two edges are brought together as will be later discussed. Although cooling wrap 10 may be used as a cold compress for application to another part of the body, it is especially intended to be worn as shown in FIG. 1 during hot weather when the user is engaged in vigorous activity such as playing tennis, performing physical labor, etc. The removal of heat from the neck area, as is well known, will give relief from some of the symptoms associated with being overheated such as feeling lightheaded, flushed, etc. Heat is removed from the neck area by cooling wrap 10 through a combination of mechanisms. Heat is not only conducted away from the neck, but also cooling wrap 10 dispenses a controlled amount of water on the neck which absorbs the heat of vaporization in evaporation. Controlled dispensing of water is desirable not only to limit the water which will reach the garments of the wearer, but also to extend the time over which cooling wrap will provide its cooling function.

Referring next to FIG. 2, the configuration of cooling wrap 10 will now be described. The cooling wrap has a single strip of fabric which is folded to form a central pouch portion 12 and a strap portion 14 at each end. As shown in FIG. 3 which is a cross-section of the strap portion, the edges of the fabric strip are folded in two times, the folded edges brought together and sewed with stitches 16. The end of each strap portion is also stitched closed. The fabric strip used to form the cooling wrap may be about 18 to 25 cm wide (7 to 10 inches) and from about 80 to 92 cm long (31 to 36 inches). This provides for straps of about 23 cm long (9 inches) and a pouch portion which may be varied to accommodate different sized necks, and may range from 34 to 46 cm long (13 to 18 inches).

The pouch portion 12 of the cooling wrap contains bag 18 (shown in cross-section in FIG. 4). Bag 18 is elongated so as to extend the length of the pouch portion of the cooling wrap. Bag 18 has closure means 20, which in this embodiment is a zipper. Contained in bag 18 is open-pored foam pad 22. Pad 22 and bag 18 are secured to the pouch portion 12 of the cooling wrap by stitches 24 along both sides of bag 18.

Bag 18 is provided to receive a frozen water medium, which, in the simplest embodiment would be ice cubes or crushed ice. It is preferred, however, that the frozen water medium used be open-pored foam which has been saturated with water and then frozen. This "frozen foam" absorbs heat more slowly than a plain ice cube and retains the resulting water for a longer time. That is, when an ice cube melts, the water is released immediately to foam pad 22 in bag 18, and from there to the fabric of the cooling wrap and the neck of the user. The water in the frozen foam is retained by the foam and is released as evaporation occurs from the cooling wrap and the neck of the wearer. Once the frozen water medium is placed in bag 18 and the closure 20 is secured, the opposite edges of the bag are brought together and held in place, for example by cooperating bristly fastening means 19 and 21 thereby forming juncture line 11 of FIG. 1.

FIG. 5 depicts a simple configuration for the frozen foam. Cubes 26 of open-pored foam are strung together on line 28 which will maintain the proper number of cubes 28 together while being frozen and transfered to bag 18. Line 28 also helps to position cubes 28 within bag 18. In lieu of cubes 26, FIG. 6 shows banana shaped open-pored foam members 30 which may be used within the cool wrap. Foam members 30 are formed to permit the cooling wrap to be curved to conform to the wearer's neck even while foam members 30 have been saturated with water and frozen. Foam members 30 may be separate or may be connected by vinyl string 32.

It should be recognized that the purpose of this invention is to comfort the wearer during vigorous activity and help prevent heat exhaustion, dizziness, etc. Consequently it is desired that some thermal insulation be provided between the neck of the wearer and the ice or frozen foam contained in bag 18 (FIGS. 2 and 4) to avoid the discomfort associated with extremely cold temperatures. This is one function of foam pad 22. It is also desirable not to have a flow of water running down the neck of the wearer. Foam pad 22 also controls the dispensing of water to the neck of the wearer to an amount which will keep the neck damp with minimal dripping. It does this by its thermal insulation aspect because it lowers the rate of heat transfer from the neck of the wearer to the frozen water medium. It also does this because its porous nature restricts the flow of water therethrough. This controlled or regulated flow of water is also enhanced when the frozen foam is used. A degree of additional control is afforded by using black or white foam so that heat transfer by radiation is accelerated or retarded. Because the pouch section of the cooling wrap is long enough to encircle the neck of the wearer (assuming a cooling wrap of the proper length has been selected) once the cooling wrap is tied in place, it will remain positioned about the neck even during vigorous activity.

As an example of the efficacy of the invention, approximately 110 grams of ice placed in the cooling wrap will last about one hour in a temperature of 90 degrees Fahrenheit. Moreover, additional quantities of ice or frozen foam can be carried in an insulated container for use when needed.

Although a cooling wrap in accordance with the invention has been illustrated and described, it will be evident that changes and modifications can be made without departing from the spirit of the invention and the scope of the appended claims.

I claim:

1. A cooling wrap comprising:
    an elongated strip of water pervious fabric forming a central pouch section with tying straps at both ends;
    said pouch section being formed by a single fold of the sides of said strip of fabric and said tying straps being formed by stitching said single folds together;
    an elongated bag formed of water pervious fabric secured in said pouch section;
    said bag having an open-pored foam liner along at least one side; and
    closure means for said bag, whereby said cooling wrap may be tied around a portion of the body and a frozen water medium placed in said bag will have body heat transferred thereto resulting in a controlled dispensing of water through said foam liner and fabric to said body portion.

2. A cooling wrap in accordance with claim 1 wherein:
    said elongated strip of fabric is at least 80 cm long and at least 18 cm wide.

3. A cooling wrap in accordance with claim 1 wherein:
    said bag is secured in said pouch section by stitching each side of said bag to the adjacent single fold of said strip of fabric.

4. A cooling wrap in accordance with claim 1 wherein:
    said closure means for said bag is a zipper.

5. A cooling wrap in accordance with claim 1 further including:
    cooperating fastening means on opposite sides of said pouch section, whereby said bag may be enclosed in a fold of said pouch.

6. A cooling wrap in accordance with claim 6 wherein:
    said cooperating fastening means is a bristly fastening means.

7. A cooling wrap in accordance with claim 1 further including:
    removable open-pored foam means, whereby said foam means may be saturated with water and frozen to serve as said frozen water medium.

8. A cooling wrap in accordance with claim 7 wherein:
    said foam means is a plurality of foam blocks.

9. A cooling wrap in accordance with claim 7 wherein:
    said foam means is a unitary member which can be shaped to conform to a neck.

10. A cooling wrap for tying about the neck of a wearer comprising:
    a strip of water pervious fabric at least 80 cm long and at least 18 cm wide forming a central pouch section with tying straps at both ends;
    said pouch section being formed by a single fold of the sides of said strip of fabric and said tying straps being formed by stitching said single folds together;
    an elongated bag formed of water pervious fabric;
    said bag having an open-pored foam liner positioned along its bottom;
    each single fold of said strip of fabric in the pouch section being stitched to one side of said bag and one side of said liner in the bottom of said bag;
    said bag having a zipper closure along its top; cooperating bristly fastening means secured to opposite sides of said pouch section of said strip of fabric; and
    a removable open-pored foam insert, sized to fit within said bag, whereby said foam insert may be saturated with water, frozen and placed in said bag to serve as a frozen water medium for absorbing body heat and controlled dispensing of water.

* * * * *